United States Patent
Culpepper et al.

(10) Patent No.: US 12,259,376 B2
(45) Date of Patent: Mar. 25, 2025

(54) METHODS AND APPARATUS FOR EVALUATING AGRICULTURAL MATERIAL WITH AN IMAGING DEVICE

(71) Applicant: DEERE & COMPANY, Moline, IL (US)

(72) Inventors: Bret M. Culpepper, West Des Moines, IA (US); James M. Hershbarger, LeClaire, IA (US); James K. Pettit, Urbandale, IA (US); Steven Coughlen, Geneseo, IL (US)

(73) Assignee: Deer & Company, Moline, IL (US)

(*) Notice: Subject to any disclaimer, the term of this patent is extended or adjusted under 35 U.S.C. 154(b) by 324 days.

(21) Appl. No.: 17/304,979

(22) Filed: Jun. 29, 2021

(65) Prior Publication Data

US 2022/0412936 A1    Dec. 29, 2022

(51) Int. Cl.
*G01N 33/02* (2006.01)
*A01D 41/127* (2006.01)
*G01N 21/88* (2006.01)
*H04N 23/52* (2023.01)
(Continued)

(52) U.S. Cl.
CPC ....... *G01N 33/025* (2013.01); *A01D 41/1277* (2013.01); *G01N 21/8851* (2013.01); *H04N 23/52* (2023.01); *H04N 23/80* (2023.01); *G01N 33/0098* (2013.01)

(58) Field of Classification Search
CPC .. G01N 33/025; G01N 33/02; G01N 21/8851; G01N 33/0098; G01N 21/3563; G01N 2021/6439; A01D 41/1277; H04N 23/52; H04N 23/51; H04N 23/80; H04N 23/00; G06V 10/12
See application file for complete search history.

(56) References Cited

U.S. PATENT DOCUMENTS

| | | | |
|---|---|---|---|
| 10,172,285 B2 | 1/2019 | Sierra et al. | |
| 2007/0079842 A1* | 4/2007 | Glynn, Jr. | A45D 20/00 132/108 |
| 2015/0321621 A1 | 11/2015 | Van Dan Elzen et al. | |

(Continued)

FOREIGN PATENT DOCUMENTS

| | | |
|---|---|---|
| CN | 109499276 A | 3/2019 |
| DE | 102004057322 A1 | 6/2006 |

(Continued)

OTHER PUBLICATIONS

Extended European Search Report and Written Opinion issued in European Patent Application No. 22177640.4, dated Mar. 2, 2023, in 11 pages.

*Primary Examiner* — Jennifer D Bennett
*Assistant Examiner* — Erin R Garber
(74) *Attorney, Agent, or Firm* — Hanley, Flight & Zimmerman, LLC

(57) ABSTRACT

In one example, a system for evaluating an agricultural material is provided. The system comprising: a housing having a passage in or through an interior of the housing with an inlet for receiving agricultural material and an outlet for outputting the agricultural material; a wall opening in a wall of the passage; and an imaging device having a window located within a border, the imaging device having a removable portion with at least one of a moisture absorbing material, a heat source, and an anti-fog agent within the removable portion.

23 Claims, 9 Drawing Sheets

(51) Int. Cl.
*H04N 23/80* (2023.01)
*G01N 33/00* (2006.01)

(56) References Cited

U.S. PATENT DOCUMENTS

| | | | |
|---|---|---|---|
| 2016/0100083 A1* | 4/2016 | Harrison | F16C 11/0609 |
| | | | 348/373 |
| 2017/0010232 A1* | 1/2017 | Daamen | G01N 21/8851 |
| 2017/0112056 A1* | 4/2017 | Sierra | A01D 61/00 |
| 2020/0314311 A1* | 10/2020 | Liu | B60R 11/04 |
| 2021/0170995 A1* | 6/2021 | Zhuang | G03B 17/02 |
| 2021/0250484 A1* | 8/2021 | Wang | H05B 1/0227 |
| 2022/0091483 A1* | 3/2022 | Low | H04N 23/55 |
| 2022/0163751 A1* | 5/2022 | Park | G02B 7/021 |
| 2022/0247896 A1* | 8/2022 | DiVirgilio | G06K 7/10821 |
| 2023/0240522 A1* | 8/2023 | Sheffield | A61B 1/126 |
| | | | 134/6 |

FOREIGN PATENT DOCUMENTS

| | | |
|---|---|---|
| EP | 1369173 A1 | 12/2003 |
| EP | 3158849 A1 | 4/2017 |
| JP | 2001322682 A | 11/2001 |
| WO | WO 2020087925 A1 | 5/2020 |

* cited by examiner

METHODS AND APPARATUS FOR EVALUATING AGRICULTURAL MATERIAL WITH AN IMAGING DEVICE

CROSS-REFERENCE TO RELATED APPLICATION(S)

Not applicable

STATEMENT OF FEDERALLY SPONSORED RESEARCH OR DEVELOPMENT

Not applicable.

FIELD OF THE DISCLOSURE

This disclosure relates to an apparatus, method and system for evaluating an agricultural material, such as an imaging system for evaluating samples of agricultural material.

ABBREVIATIONS

Abbreviations appearing relatively infrequently in this document are defined upon initial usage, while abbreviations appearing more frequently in this document are defined below:

BACKGROUND OF THE DISCLOSURE

This disclosure relates to a system for evaluating an agricultural material, such as an imaging system for evaluating samples of the agricultural material. The moisture value of bulk grain may depend upon the quality of the bulk grain. High quality grain is reflected by high percentages of clean unbroken grain and low percentages of broken grain and maternal other than grain (MOG). Monitoring the quality of bulk grain is often difficult and subject to error. Certain imaging systems use imaging devices positioned at various places on a combine for collecting images of an agricultural material. The window and/or a lens of the camera may become obscured or affected by internal or external moisture (fogging) debris, dirt, dust or other contaminants that impacts detrimentally the accuracy of the evaluation of images of the agricultural material. In some imaging systems, an operator or technician can clean the window of the camera only by time-consuming disassembly of the imaging system from the combine with tools, such as wrenches. Accordingly, there is need for a system for evaluating agricultural material that resists fogging of the window of the camera, such as in real-time in the field.

SUMMARY OF THE DISCLOSURE

In one example, a system for evaluating an agricultural material is provided. The system comprising: a housing having a passage in or through an interior of the housing with an inlet for receiving agricultural material and an outlet for outputting the agricultural material; a wall opening in a wall of the passage; and an imaging device with a removable portion, the removable portion having at least one of a moisture absorbing material, a heat source and an anti-fog agent, the removable portion acting to reduce obscuring of an associated window of the imaging device.

In another example, apparatus for evaluating an agricultural material, the apparatus comprising: a removable portion configured to interface with an imaging device, the removable portion having at least one of a moisture absorbing material, a heat source, and an anti-fog agent to reduce fogging of a window of the imaging device due to a temperature differential between the agricultural material and the imaging device.

In yet another example, a system for evaluating an agricultural material, the apparatus comprising: an imaging device having a window located within a border, wherein the imaging device is pivotally mounted for rotation with respect to a housing through which the agricultural material passes such that in a closed state the border rests on, engages or interlocks with a wall opening in the housing, and in an open state the border exposes the wall opening and the interior of the housing; and a removable portion interfacing with the imaging device, the removable portion having at least one of an moisture absorbing material, a heat source and an anti-fog agent within the removable portion.

BRIEF DESCRIPTION OF THE DRAWINGS

At least one example of the present disclosure will hereinafter be described in conjunction with the following figures.

For simplicity and clarity of illustration, descriptions and details of well-known features and techniques may be omitted to avoid unnecessarily obscuring the non-limiting examples described in the subsequent Detailed Description. It should further be understood that features or elements appearing in the accompanying figures are not necessarily drawn to scale unless otherwise stated.

DETAILED DESCRIPTION

Examples of the present disclosure are shown in the accompanying figures of the drawings described briefly above. Various modifications to the examples may be contemplated by one of skill in the art without departing from the scope of the present disclosure, as set-forth in the appended claims.

Figure 1:
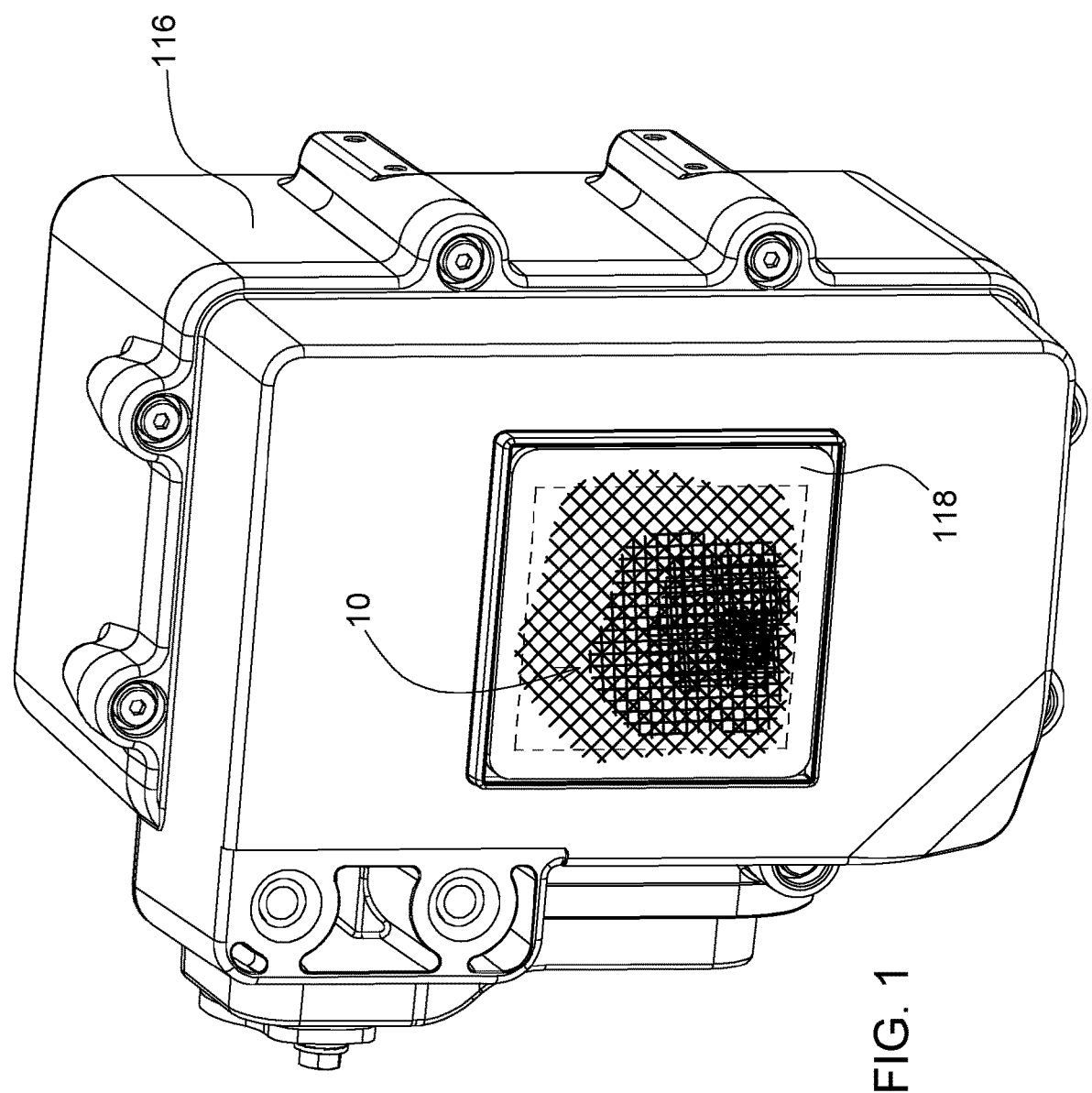
FIG. 1 is a perspective view of an imaging device with fogging of the window.

Certain imaging systems as shown FIG. 1 use imaging devices that are positioned at various places on a combine for collecting images of an agricultural material. One example of an imaging system is disclosed in U.S. Pat. No.

10,172,285, which is incorporated by reference in its entirety. For example, an imaging device may be placed on a bypass channel on a clean grain elevator of a combine. The window of the imaging device may become obscured or affected by internal or external moisture, fogging, debris, dirt, dust or other contaminants (see 10 in FIG. 1) that impacts detrimentally the accuracy of the evaluation of images of the agricultural material. Further, the internal circuitry and/or components of the imaging device may become corroded due to internal or external moisture, fogging, debris, dirt, dust or other contaminants. In some imaging systems, an operator or technician can clean the window of the camera only by time-consuming disassembly of the imaging system from the combine with tools, such as wrenches. In accordance with one example, a system for evaluating agricultural material is provided that resists, for example, fogging 10 of the window of the camera, such as in real-time in the field.

Exemplary System for Evaluating an Agricultural Material

Figure 2:
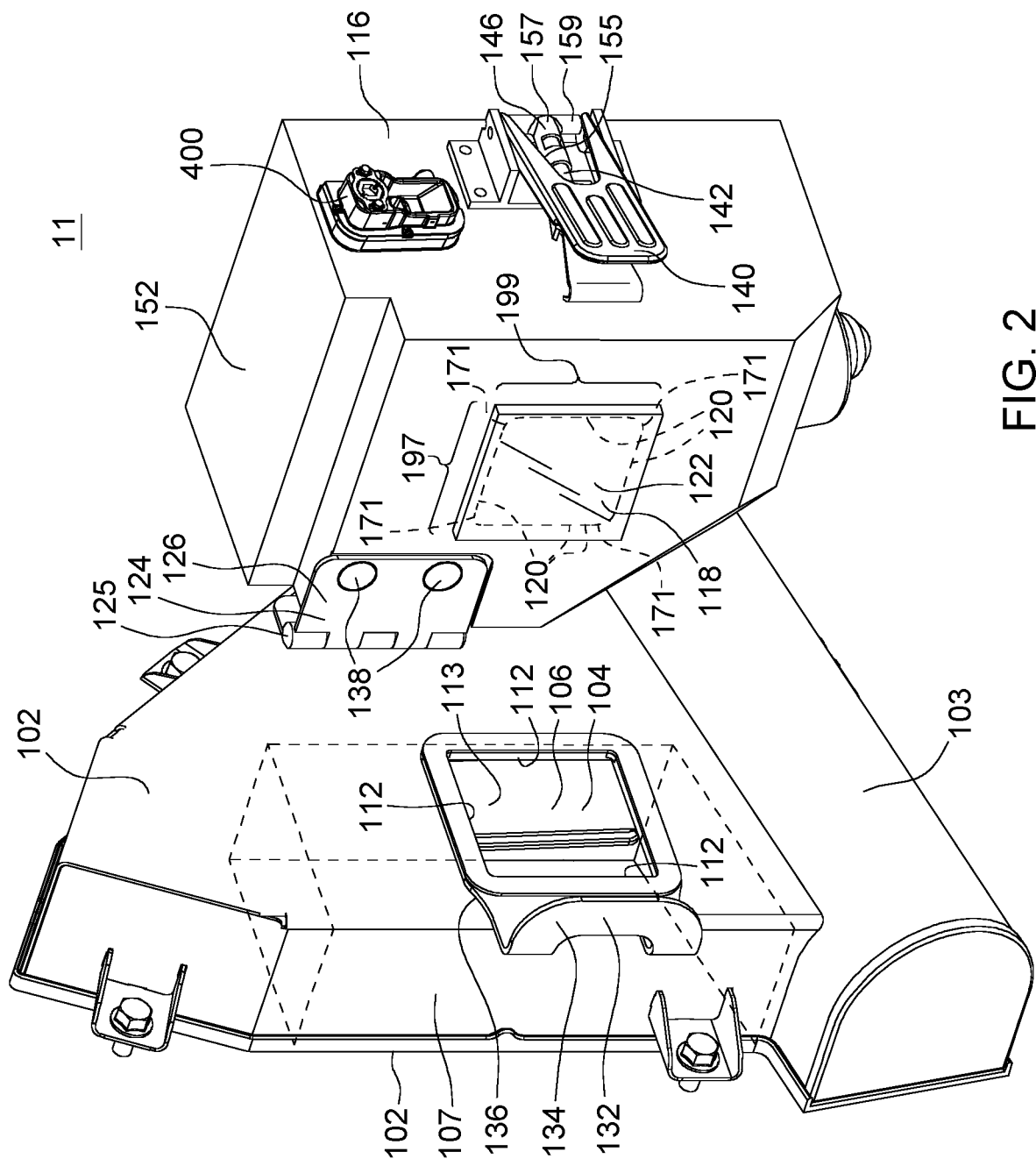
FIG. 2 is a perspective view of the system for evaluating an agricultural material where the imaging device is an open state and showing an opening in the housing.
Figure 3:
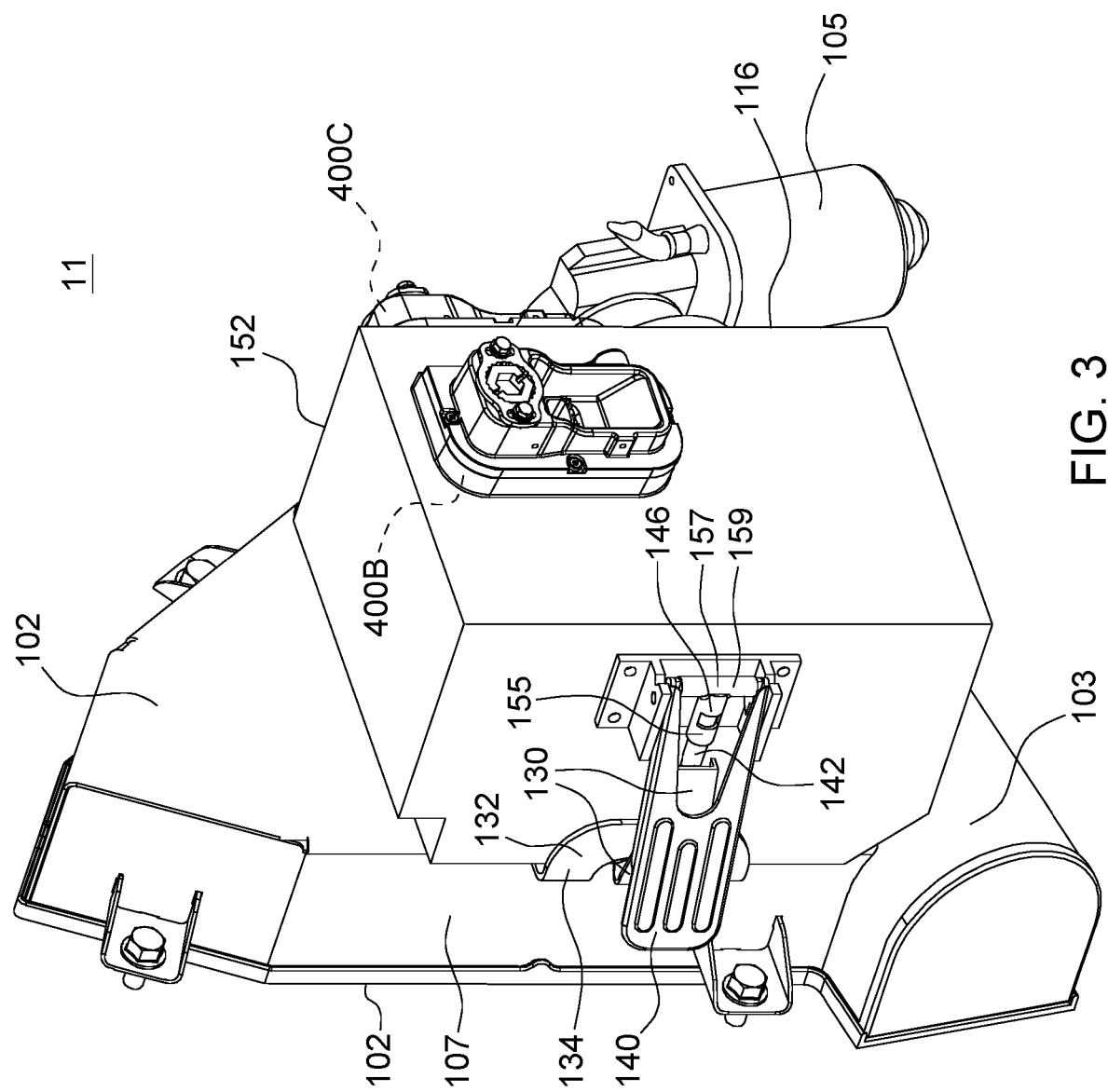
FIG. 3 is a perspective of the system for evaluating the agricultural material where the imaging device is in a closed state and positioned proximate the opening in the housing of FIG. 1.
Figure 4:
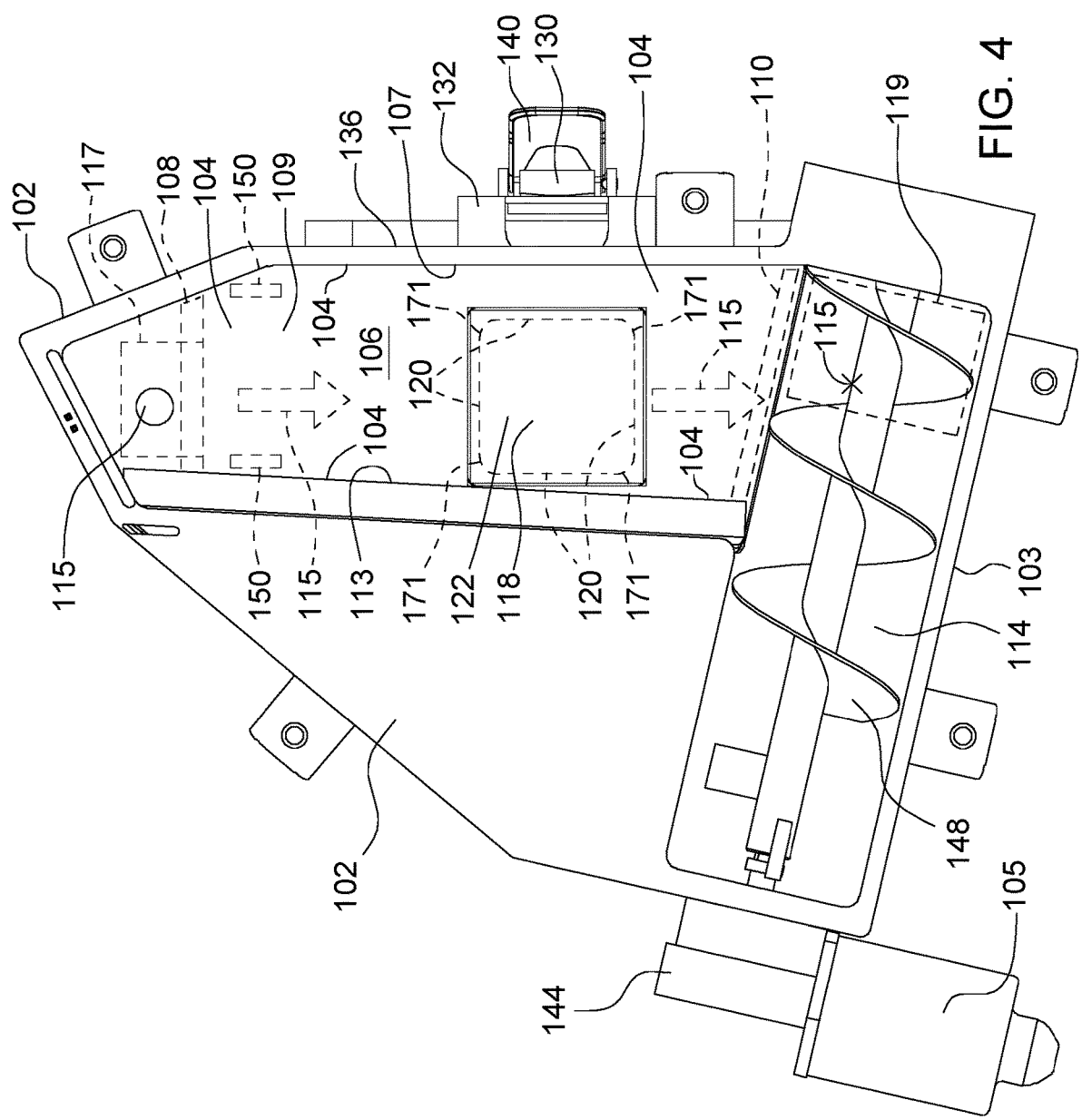
FIG. 4 is a side view of system for evaluating the agricultural material where in the imaging device is positioned in the closed state and an auger is exposed.

FIGS. 2 and 3, inclusive, illustrate a system 11 for evaluating the agricultural material. Agricultural material may include one or more of the following: grain, oil seed, fiber, maize, corn, cereal, forage material, sugar cane, soybean, wheat, oats, barley, rye or other plant material that is edible, or used for any other industrial or commercial purpose. The system 11 comprises a housing 102 having a passage 104 in or through an interior 106 of the housing 102 with an inlet 108 for receiving agricultural material and an outlet 110 for outputting the agricultural material to an auger 148 or other device for conveying agricultural material. As best illustrated in FIG. 4, the inlet 108 may lie in a plane that is substantially perpendicular to the plane of the sheet of FIG. 4; the outlet 110 may lie in a plane that is substantially perpendicular to the plane of the sheet of FIG. 4 and spaced apart from (e.g., substantially parallel to) the inlet 108. In one example, the inlet 108, the outlet 110, or both occupy the full cross-sectional dimension of the passage 104.

In one example, a passage 104 may comprise a channel or bypass channel that bypasses an elevator 12 (e.g., an elevator or clean grain elevator in FIG. 8) for transporting agricultural material from a container (e.g., a grain bin) of the combine, harvesting machine, agricultural equipment, or heavy equipment to a chute or spout for unloading agricultural material from the container. For example, an elevator inlet of the elevator 12 is gravity fed from the container or coextensive with a bottom of the container, whereas the top or outlet of the elevator is associated with the chute or spout for unloading or transferring the agricultural material from the harvesting machine or combine. Alternately, the elevator inlet of the elevator 12 is fed by the output of desired portion of agricultural material that harvested, obtained or separated by the combine system 100.

The passage 104 is associated with a housing 102 that is attached to the elevator (e.g., clean grain elevator), a combine, a harvester or another vehicle. In one example, the passage 104 may be defined by a first wall 109, a second wall 107 (e.g., an outer wall) and a third wall 113 (e.g., interior wall), and an adjacent wall (not shown), such as an elevator wall or additional wall panel of the system 11. The edge or corner 151 of the third wall 113, which intersects with the first wall 109, is shown in phantom as dashed lines in FIG. 2.

Figure 8:
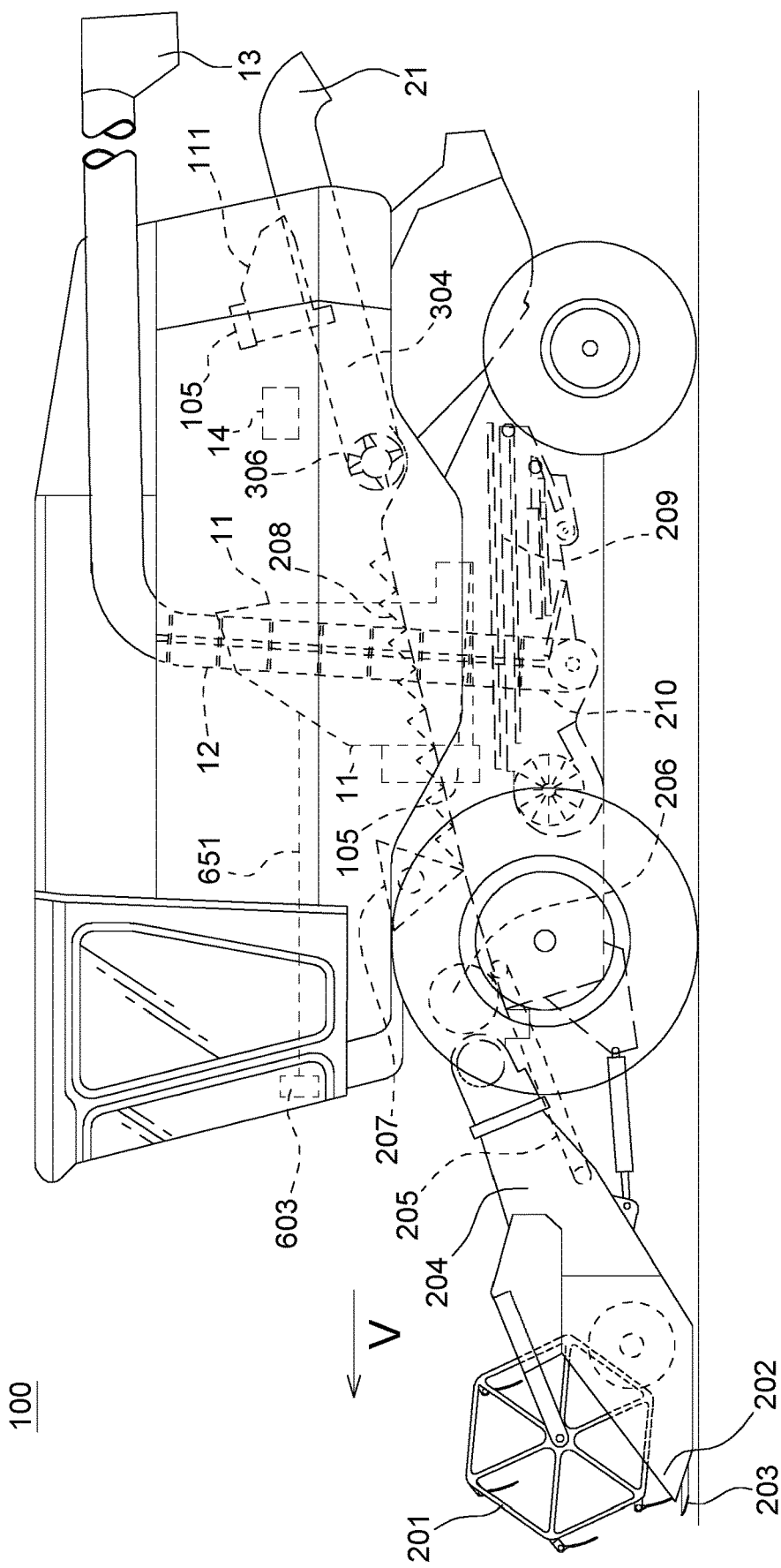
FIG. 8 is a side view of a combine or a harvesting machine with the system for evaluating the agricultural material.

Further, the elevator input region 117 receives a sampled portion or diverted portion of agricultural material (e.g., as shown in FIG. 4 and FIG. 8) that is moving (e.g., upward) in the grain elevator 12, where the sampled portion of the agricultural material moves or flows (e.g., downward) through the passage 104 on a gravity fed basis to an auger that is in communication with the elevator output region 119, where the sampled portion of agricultural material enters or re-enters the elevator 12 to be conveyed (e.g., upward). In practice, the elevator input region 117 and the elevator output region 119 correspond to a first elevator opening and a second elevator opening in elevator 12, respectively. The elevator input region 117 is aligned or registered with the inlet 108 of the system 11, whereas the elevator output region 119 is aligned or registered with the outlet 110 of the system 11. In the passage 104, the direction of the flow 115 of the agricultural material is indicated by the arrows, the dot with a concentric circle, and the X symbol, through the passage 104 between the elevator input region 117 and the elevator output region 119, where the dot with the concentric circle indicates flow 115 of the agricultural material into the plane of the drawing of FIG. 4 and the X symbol indicates a flow 115 of the agricultural material outward from the plane of the drawing of FIG. 4.

In one example, a wall opening 112 is in a first wall 109 of the passage 104. For example, the wall opening 112 is in a substantially vertical first wall 109 of the passage 104. In one example, the wall opening 112 may comprise a substantially rectangular opening, although the wall opening 112 may be substantially elliptical, circular, polygonal, or have another geometric shape. Similarly, the window 118 and its border 120, collectively or individually, may be substantially rectangular, elliptical, circular, or polygonal, among other possibilities. As illustrated in FIG. 2 and FIG. 4, the window 118 (or window) may have rounded corners 171 or tapered or chamfered edges to reduce stress on the window 118, such as mechanical stress that can result from differential thermal coefficients of expansion in the material of the window 118 with respect to the material (e.g., metal, alloy, polymer, plastic, or fiber-filled plastic or polymer) of the border 120 or frame. The rounded corners 171 or tapered or chamfered edges facilitate the window's survival of extreme temperature fluctuations without cracking or other damage from thermal or mechanical stress.

The opening size and opening shape of the wall opening 112 is generally commensurate with: (1) the size and shape of the window 118 of the imaging device 116, or (2) the size and shape of a border 120 of or around the window 118. As referenced in this document, the window 118 may comprise polycarbonate plastic, acrylic plastic, glass, quartz, or other structure that is substantially planar, a plate, substantially convex or rectilinear, with or without optical magnification or focusing; further, such window 118 may comprise a secondary window (e.g., lens 702 in FIG. 7) that is part of a compound window if the secondary window is spaced apart from a primary window 118 of the imaging device 116. The wall opening 112 may have a thickness, shelf, ledge, mating surface or recessed mating surface for receiving the window 118 or translucent plate of the imaging device 116, or for receiving a frame or border 120 surrounding the window 118 or translucent plate of the imaging device 116. In one example, the frame or border 120 may protrude outward (e.g., axially, radially or both from an optical or geometric central axis of the window) from the window 118 or translucent plate, wherein the frame or border 120 engages, interlocks or mates with the wall opening 112, or its thickness, periphery, shelf, ledge, mating surface, or mating recess surface.

In one example, an imaging device 116 comprises a camera, charged-coupled device, an image sensor (e.g., 704 in FIG. 7), a complementary metal-oxide-semiconductor (CMOS) imaging device, or another device for capturing one or more images, a sequence of images, or video of the agricultural material in the passage 104. The imaging device 116 may operate within one or more of the following light spectrum ranges or corresponding frequency ranges: visible light spectrum, near-infrared light spectrum, infra-red light spectrum and ultraviolet light spectrum. The imaging device 116 may measure transmittance, reflectance of light within one or more spectrum or frequencies to estimate attributes or characteristics of the agricultural material. Attributes or characteristics of the agricultural material may include any of the following: oil content, protein content, moisture content, yield, damaged grain, and foreign materials in the agricultural material, pesticide resistance, herbicide resistance, genetically modified attributes, or other attributes. Further, the imaging device 116 may be used in conjunction with other sensors, such as microwave moisture sensors, yield monitors, and other devices to estimate the values of or presence of attributes or parameters of the agricultural material.

In one example, the imaging device 116 comprises an enclosure 152 with a window 118 or translucent plate that can face the passage 104 to view the moving or stationary agricultural material in the passage 104. An imaging device 116 has a window 118 or translucent plate of the imaging device 116 located inward (e.g., radially inward) from a border 120 or frame of the imaging device 116. The imaging device 116 is pivotally mounted for rotation with respect to housing 102 such that in a closed state the border 120 (or the window 118) engages or interlocks the wall opening 112. In an open state, which is illustrated in FIG. 2, the removal of the border 120 or window 118 from the wall opening 112 exposes the wall opening 112 and an interior 106 of the passage 104 to facilitate rapid, convenient and accessible cleaning of debris or other material from the passage 104, without removal of the imaging device 116 from the system 11 or equipment, and without use of any tools (e.g., wrenches, screwdrivers, pliers or otherwise). In the open state an operator, technician or other person can remove quickly and readily clogged agricultural material or other material that blocks, clogs or accumulates in the passage 104. In one example, in the open state the window 118 surface that faces the interior 106 of the housing 102 is exposed to facilitate rapid, convenient and accessible cleaning of debris, dirt, mud, smudges, insects, vermin, or other material from the window 118 surface, without removal of the imaging device 116 from the system 11 or equipment, and without use of any tools (e.g., wrenches, screwdrivers, pliers or otherwise). The operator, technician, or other person can quickly clean the window 118 or translucent plate of the imaging device 116 to eliminate false or inaccurate readings or analysis of the agricultural material that might otherwise occur.

FIG. 3 is a perspective view of the system for evaluating the agricultural material where the imaging device 116 and its enclosure 152 are positioned in a closed state. The imaging device 116 is pivotally mounted for rotation with respect to housing 102 such that in a closed state the border 120 (or window 118) rests on, engages or interlocks the wall opening 112. In one example, the border 120 (or window 118) contacts the opening, a mating surface of the wall opening 112 or a recessed mating surface of the wall opening 112. For instance, border 120 or frame can be generally rectangular as shown in FIG. 2 or FIG. 3, where the border 120 protrudes (e.g., axially, radially, or both) from the imaging device 116 and is inserted into the opening in the closed state.

In one example, the pivotal mounting is accomplished by a hinge 124 or hinged structure that rotates about a rotational axis or hinge pin 125. For example, the hinge 124 comprises a first hinge portion 126 and a second hinge portion 128. The first hinge portion 126 is secured to the imaging device 116 and the second portion is secured to the housing 102 via fasteners 138 or otherwise. The first hinge portion 126 and the second hinge portion 128 can rotate with respect to each other. The first hinge portion 126 and the second hinge portion 128 may have a recess (e.g., a cylindrical recess) for receiving a hinge pin 125 to support relative rotation movement of the first hinge portion 126 and the second hinge portion 128.

In one example, a latch 130 engages a keeper 132 to lock the imaging device 116 or its enclosure 152 to the housing 102 in a closed state for observation of agricultural material in the passage 104. In one configuration, the keeper 132 comprises a hook or bracket 134 that extends generally orthogonally outward from an outer surface 136 of the housing 102 or the bracket. The latch 130 is coupled to or connected to a lever 140 with an optional resilient member 146, or the latch 130 may act both as a latch 130 and a resilient member, if the latch 130 is made of a suitable material, such as spring steel. In one configuration, the lever 140 can be pivoted or rotated with respect to the latch 130 to place the latch 130 or the optional resilient member 146 under resilient tension. As illustrated, the optional resilient member 146 may comprise a coil spring that is coupled to the latch 130 at a first latch end 155 (e.g., via member 142, or a substantially cylindrical member, that is coaxially aligned with the spring) and fixed at a second latch end 157, opposite the first latch end 155, to a member 159. In one example, the latch 130 is held in a locked state by an optional resilient member 146, or the resilient latch 130 itself. The latch 130 and the lever 140 are mounted to the enclosure 152 via bracket 149.

An operator, technician or other person can move the latch 130 or the lever 140 (e.g., even without any wrench, screwdriver or other tools) to overcome the force of the optional resilient member 146 (or a resilient latch 130) to move from a closed state and locked state to an open state, where the window 118 or translucent plate, or the passage 104 is exposed or accessible for quick and convenient cleaning. In another example, the latch 130 can be associated with an auxiliary catch, or a pawl (e.g., spring-loaded pawl) and ratchet wheel, an auxiliary catch, or other retaining mechanism for holding the latch 130 and keeper 132 in locked state under resilient tension, wherein the lever 140 can release the pawl from the ratchet by overcoming the force of the optional resilient member 146 (or the resilient latch 130) to transition from the locked state to the open state.

The passage 104 may comprise a channel or bypass channel that bypasses an elevator 12 for transporting agricultural material. In one example, the passage 104 extends from an elevator input region 117 (e.g., upper opening) in the elevator 12 to an auger chamber 114, where the auger chamber 114 communicates with an elevator output region 119 (e.g., lower opening) in the elevator 12.

FIG. 4 is a side view of system 11 for evaluating the agricultural material where in the imaging device 116 is positioned in the closed state with the latch 130 engaging the keeper 132 in a locked state and where the auger 148 is exposed by showing a cut-away view of the panel covering the auger chamber 114. As illustrated, the auger chamber 114 is substantially cylindrical, where one end is driven by the motor 105 via its shaft or a gearbox 144 and the opposite end associated with a bearing (e.g., radial bearing, axial bearing, or both). The outlet 110 is open to provide or convey the agricultural material into an elevator output region 119 (e.g., lower opening) of the elevator 12. The auger chamber 114 is defined by an auger housing portion 103. As the elevator 12 operates, the elevator 12 conveys agricultural material upward toward the chute, the elevator input region 117, and the inlet 108, which receives a sampled portion or diverted portion of the agricultural material. When the passage 104 is adequately, partially, or substantially filled, with agricultural material, the imaging device 116 may take one or more images (e.g., still images, a sequence of images, or motion picture images) of the agricultural material for evaluation of the attributes or characteristics of the agricultural material.

Removable Portion

Additionally, FIGS. 2 and 3 disclose an imaging device 116 comprising a removable portion 400 for preventing or resisting internal or external moisture (fogging), debris, dirt, dust or other contaminants (see 10 in FIG. 1) of window 118 that impacts detrimentally the accuracy of the evaluation of images of the agricultural material. Removable portion 400, in combination with an associated humidity sensor (not shown) of circuit board 706, may also prevent or resist corrosion of internal circuitry and/or components of the imaging device due to internal or external moisture (fogging) debris, dirt, dust, or other contaminants of a circuit board 706 of imaging device 116. The removable portion 400 may be configured with at least one of a moisture absorbing material, a heat source, and an anti-fog agent. The removable portion may also be removably attached at one or more positions of the imaging device 116, including for example a side wall (e.g., 400 of FIG. 2 or 400C of FIG. 3) or a back wall (400B of FIG. 3), so long as the position does not interfere the operation of imaging device 116. As shown in FIG. 3, it can also be appreciated that one or more removable portions (400B, 400C) are positioned at one or more locations (400B, 400C) as needed by the specific usage of the imaging device 116.

In one example, the removable portion 400 is customer facing and removable without disassembly of the imaging device to which it is attached. In another example, removable portion 400 comprises a drying agent or moisture absorbing material within a separate replaceable cartridge 406 (best seen in FIG. 6) held in place by an anti-rotation bracket 407 and fasteners 408 to the removable portion 400. Anti-rotation bracket 407 in one example consists of 24 point grooves to securely retain and prevent rotation of the cartridge 406 having a hex head configuration. In yet another example, cartridge 406 comprises one or more commercially available desiccant cartridges or plugs (e.g., TROPACK Packmittel GmbH or Farpoint FP329 Desiccant Plug) having, for example, an internal molecular sieve or silica gel desiccant, the cartridge 406 capable of being threaded into one or more areas on removable portion 400. Further, cartridge 406 may work in conjunction with additional moisture absorbing materials within removable portion 400 and/or within imaging device 116. In this example, removable portion 400 and/or cartridge 406 may have an indicator (e.g., a visual indicator such as orange indicating silica gel) identifying when the cartridge 406 should be removed and replaced with a new cartridge 406. It can be appreciated by one of ordinary skill, that any number and type of indicators (e.g., visual, audio, otherwise) may be utilized to convey information about the life of the moisture absorbing materials within a cartridge 406. It is expected that cartridge 406 (and thus the life indicator of the moisture absorbing materials therein) last at least one season of use and thus will be removed and replaced once per year. However, it can be appreciated by one of skill in the art that the life of cartridge 406 may vary depending upon usage. In these examples, removable portion 400 acts—alone or in combination with another moisture absorbing material—to remove excess moisture within the internal cavity(ies) of imaging device 116. Removable portion 400 thus reduces the likelihood of fogging of window 118 created by the temperature differential between the imaging device 116 and the agricultural material within passage 104.

In another example, removable portion 400 is configured with a heat source for raising the temperature of window 118 of imaging device 116. In this example, removable portion 400 has an electrically powered heating coil that interacts with at least a periphery of window 118. Alternatively, or additionally, the electrically powered heating coil could interact with housing 102 to add more indirect heating of the agricultural material within passage 104 before window 118. Removable portion 400 being configured to heat up certain agricultural material, directly or indirectly, within passage 104 of housing 102 to within an acceptable range (e.g., within 10 degrees F.) relative to window 118. In this manner, removable portion 400 interacts with at least one of the window 118, imaging device 116 and housing 102 to raise a temperature of the window 118 and/or agricultural material within passage 104 and reduce a temperature differential. By reducing the temperature differential between the imaging device 116 and the agricultural material, the potential for fogging of window 118 would also be reduced.

In still yet another example removable portion 400 is configured to activate, dispense, or apply an anti-fog agent, coating, or filter. For example, the removable portion 400 may activate an anti-fog coating or filter—such as a commercially available anti-fog filter from Advanced Nanotechnologies—that is applied to an inside surface of window 118 of the removable portion 400 to reduce the likelihood of fogging. In this example, upon activation, the anti-fog agent will allow for 100% transmittance and neutrality across the IR and visual spectrum such as to not interfere with the operation of imaging device 116.

Figure 5:
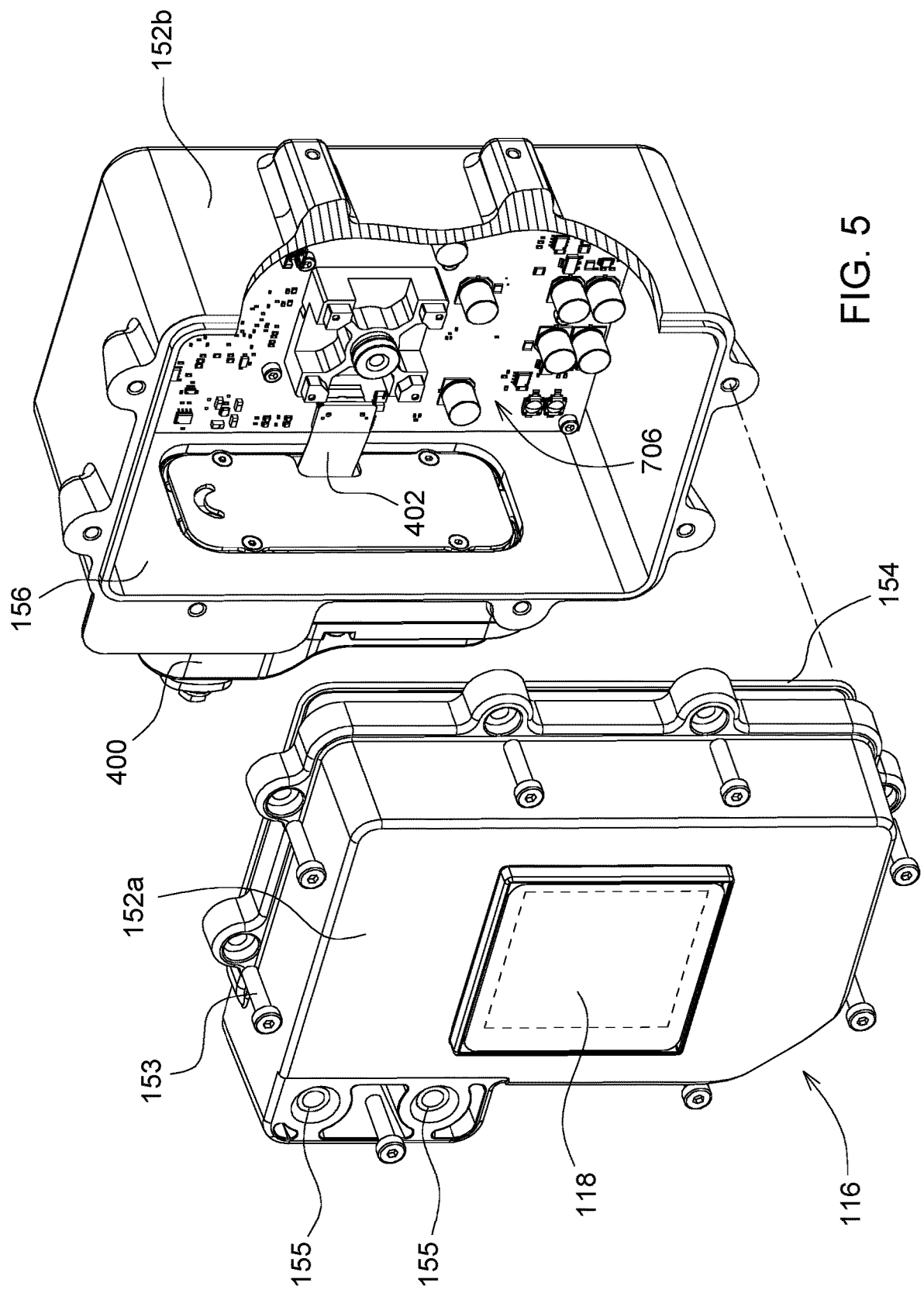
FIG. 5 is an exploded perspective view of the system for evaluating the agricultural material.

Referring now to FIG. 5, an exploded perspective view of the system for evaluating the agricultural material is shown. In this example, enclosure 152 is comprised of a top section 152a and bottom section 152b secured together by a plurality of fasteners 153 around a periphery of the top and bottom sections 152a, 152b. A gasket 154 may be positioned between top section 152a and bottom section 152b to create a generally waterproof, dustproof seal. Top section 152a has disposed within it the window 118 that can face the passage 104 to view the moving or stationary agricultural material in the passage 104. Top section 152a further having a pair of apertures 155 into which fasteners 138 (see FIG. 2) can be inserted for hinged movement of imaging device 116.

With respect to bottom section 152b, circuit board 706 is disposed proximate a bottom surface (i.e., opposite window 118). Removable portion 400 is attached to one or more of the sidewalls of bottom section 152b with a plurality of fasteners 408 (FIG. 6) and gasket 154 to create a generally waterproof, dustproof seal. However, in one example, removable portion 400 is positioned along a sidewall 156 such that a ribbon cable 402 extends through base plate 412 and can be connected at a first end to circuit board 706. Ribbon cable 402 may also have a second end connected to communications port 404 (best seen in FIG. 6) allowing for powering of imaging device 116 and transmission of collected image data from imaging device 116 to a connected device in, for example, an operator cab of a combine harvester.

Figure 6:
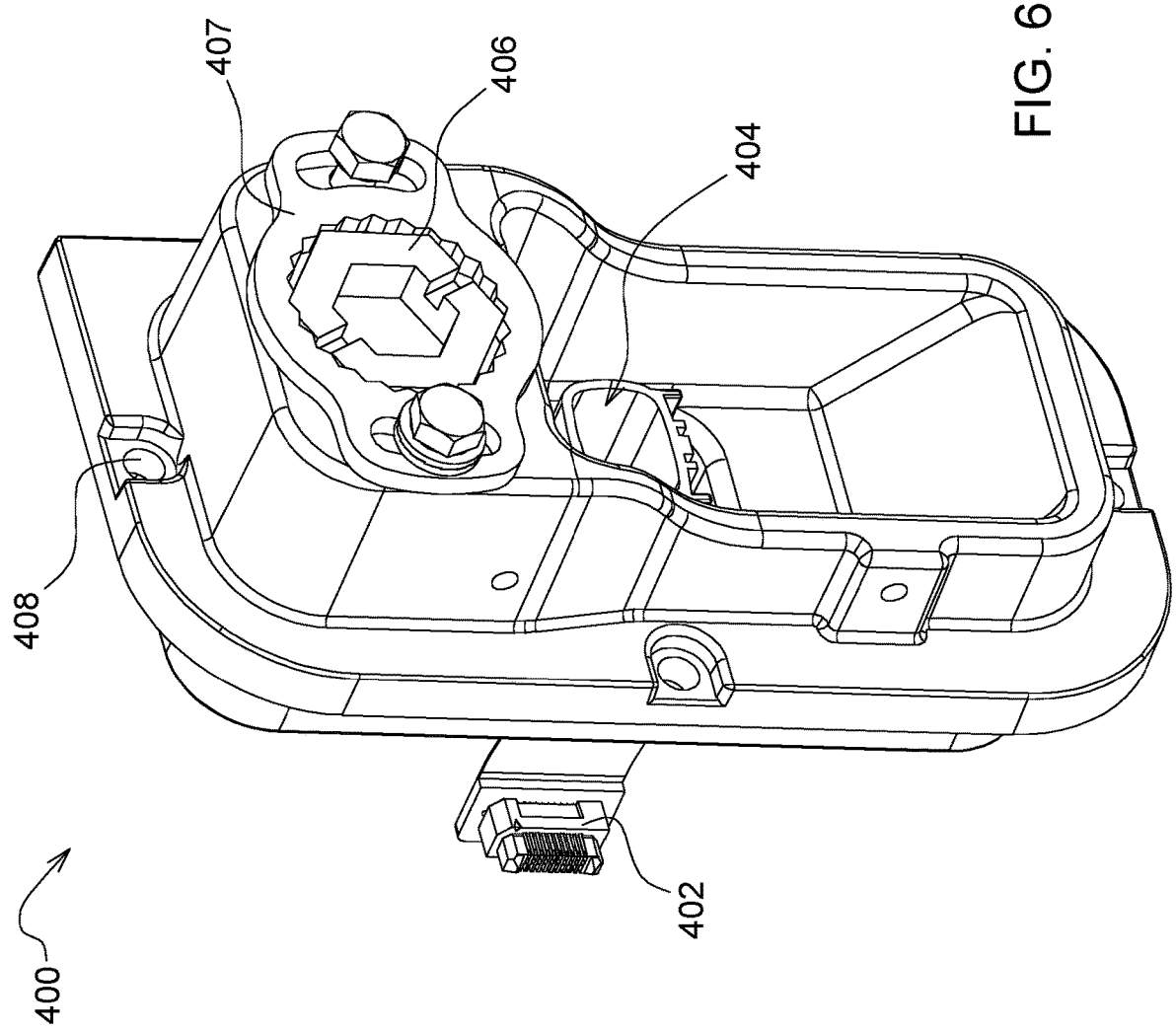
FIG. 6 is an exploded perspective view of a removable portion of the system for evaluating the agricultural material.

FIG. 6 is an exploded perspective view of a removable portion 400 of the system for evaluating the agricultural material. In one example, removable portion 400 is attached by a plurality of fasteners 408 to a sidewall 156 of bottom section 152*b*. Removable portion 400 may be positioned proximate to a communications port 404 allowing for electrical connection and transmission to another connected device on a combine. As previously discussed, removable portion 400 is removable without disassembly of the imaging device to which it is attached. In one example, there is a separate cartridge 406 removably attached to or, alternatively, threaded into a customer facing side of the removable portion 400. For example, a desiccant cartridge (e.g., TROPACK Packmittel GmbH or Farpoint FP329 Desiccant Plug) containing a molecular sieve or silica gel may be separately fastened to or threaded into one or more areas on removable portion 400.

Removable portion 400 may further be configured with an internal cavity formed by at least an outer housing 410 and base plate 412. Base plate 412 is fastened to outer housing 410 with a plurality of fasteners 408. Further, base plate 412 may have at least one aperture through which air can circulate between the internal cavity of removable portion 400 and the internal cavity of enclosure 152 formed by top and bottom sections 152*a*, 152*b*. In these examples, removable portion 400 acts to remove excess moisture within the internal cavity(ies) of imaging device 116 and reduce the likelihood of fogging of window 118 created by the temperature differential between the imaging device 116 and the agricultural material within passage 104.

Figure 7:
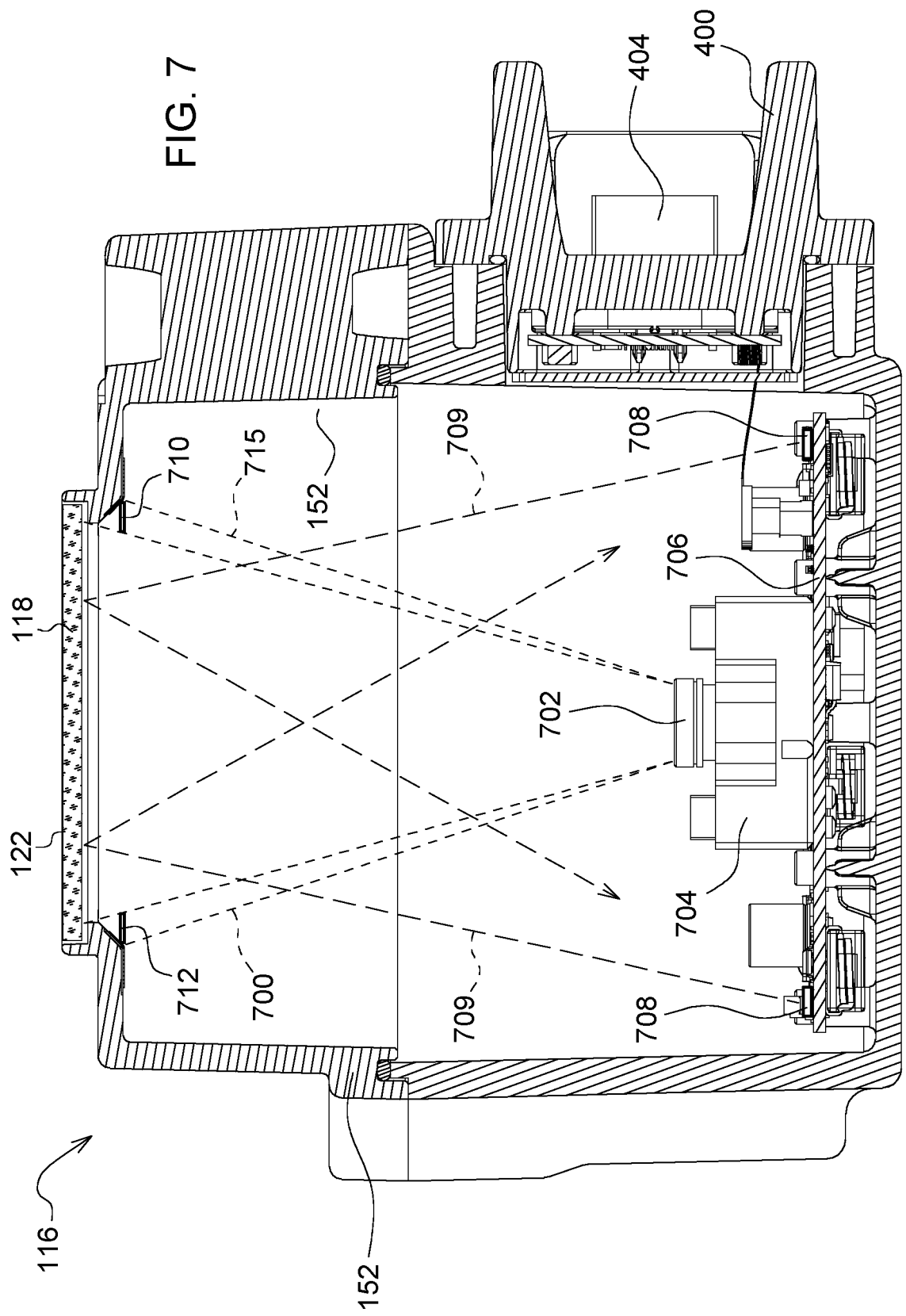
FIG. 7 is a plan view of the imaging system with a top of the enclosure removed or cut away to reveal an interior of the enclosure including the removable portion.

FIG. 7 shows a top view of the imaging device 116 with the top of the enclosure 152 removed or cut away to reveal an interior of the enclosure 152 and removable portion 400. In one example, the imaging device 116 comprises a charge-coupled device or other image sensor 704 for collecting image data related to the agricultural material in the passage 104. The image sensor 704 of the imaging device 116 faces the window 118 or window to collect image data of agricultural material in the passage 104. The image sensor 704 can detect image data within a first field of view 700 or a second field of view 715 through one or more windows (e.g., primary window 118, and a (secondary) window/lens 702) or a compound window or lens arrangement. As illustrated in FIG. 7, the image sensor 704 and associated lens 702 are mounted on a circuit board 706. Further, one or more light sources 708, such as light-emitting diodes may be mounted on or adjacent to the circuit board 706 for illuminating the agricultural material in the passage 104. The light sources 708 may comprise light sources that output one or more of the following electromagnetic radiation: visible light (e.g., white, red, blue, or green frequency bands), ultra-violet light, infra-red light, and near infra-red light.

As shown by the illustrative representation of the light path 709 from the light source 708, the light path 709 or the light sources 708 illuminate the window 118 with reduced glare because the (direct) reflections of the light path 709 from the window 118 to do not directly impinge on or strike the lens 702 or the image sensor 704. The direct (specular) reflection of the light path 709 from the window 118 excludes the region or sensing surface of the image sensor 704. Instead, the light source 708 indirectly illuminates the sensing surface of the image sensor 704 to reduce glare (e.g., and to compensate for optical attenuation from minor imperfections or scratches in the window 118 in the collected images from the image sensor 104 or imaging device 116 without complex optics or arrangement of the light source 708. The window 118 is illuminated from radiation emitted from the light sources 708 and direct reflections of the radiation do not impinge upon the image sensor 704 to reduce glare or glare-related distortion (e.g. artifacts, such as undesired reflections of portions of the interior of the imaging device 116 or discolored lighter regions of pixels) in the collected image data. As illustrated in FIG. 7, the light sources 708 are spaced apart on each side of the image sensor 704 and may be mounted on a same or common circuit board 706 or substrate as the image sensor 704. Further, in some examples, the light sources 708 may be substantially co-planar with respect to the image sensor 704 or its lens 702. For example, substantially co-planar means that the light sources 708 and the image sensor 704 are aligned, or the light sources 708 and the lens 702 are aligned such that a plane or an axis can simultaneously intercept their packages, or any of their outer surfaces. The first field of view 700 of the image sensor 704 is selected to include substantially all total window surface area 122 of the window 118 or lens 702, whereas the second field of view 715 of the image sensor 704 extends beyond the surface area (e.g., 122) of the window 118 to include reference image data (710, 712).

In one example, the reference image data (710, 712) comprises reference color pattern 710 or chart, a reference gray-scale pattern 712 or chart, or both. For example, the image sensor 704 or its associated controller 603 or data processor 604 can crop the image or change the field of view (e.g., between a first field of view 700 and a second field of view 715) or focus via an optional adjustable lens to change the field of view. During a diagnostic mode, the imaging device 116 can capture the second field of view 715 such that the controller 603 or data processor 604 can refer to the reference color pattern 710, the reference gray-scale pattern 712, and collected image data in one or more images to determine an operational or diagnostic status of the imaging device 116, or its components, such as failure of one or more light sources 708 with a known frequency versus radiation intensity output. During an operational mode that is separate from the diagnostic mode, the imaging device 116 can capture one or more images in the first field of view 700 such that the controller 603 or data processor 604 for processing to determine the characteristics or volume of the agricultural material, for example.

FIG. 8 illustrates a combine system 100 or harvesting system for harvesting grain from a field. In one example, the combine system 100 can comprise a revolving reel 201 for pushing the agricultural material (e.g., grain crop) planted in the field towards a cutter bar 203, where the cutter bar 203 comprises a plurality of teeth configured to cut off the agricultural material at or near their base. The combine system 100 further comprises a header divider 202 for defining a row of crop or material that will be harvested by the combine system 100, a feeder 204 configured to accept the agricultural material after it has been cut by the cutter bar 203, a conveyor 205 configured to transport the agricultural material from the feeder 204 to an internal chamber of the combine system 100, a threshing drum 206 configured to beat/thresh the agricultural material traveling on or provided by the conveyor 205 to break, shake or separate a desired portion (e.g., seeds, fiber or grain) of the agricultural material from an undesired portion of the agricultural material (e.g., a stalk portion or straw chaff), a beater 207 configured to further separate (e.g., beat/thresh) the agricultural material traveling on or provided the conveyor 205 into a desired portion (e.g. concentrated desired portion) and an undesired portion. In one example, an optional shaking screen 208 is configured to separate the desired portion from the undesired portion and is disposed of out of a rear outlet 21 for the undesired portion of the agricultural material, while the desired portion of the agricultural material can fall towards the sieve 209 (e.g., grain sieve). The sieve 209 further separates the desired portion (e.g., grain) of the agricultural material from any remaining undesired portion (e.g., straw chaff portions). After falling through the sieve 209, the desired portion (e.g., grain, oilseed, or fiber) of the agricultural material is collected in a container 210 (e.g., holding tank). Grain collected in the container 210 can be may be transferred to a storage container (e.g., grain wagon) traveling alongside the combine system 100, where the storage container may be arranged to hold a larger amount of grain than the container 210 within the combine system 100.

As the undesired portion of the agricultural material is collected toward the top of the sieve 209, a fan 306 or rear conveyer moves, propels or forces the undesired portion of the agricultural material (e.g., tailings) into passage 304 for exit at the rear outlet 21, or prior to exit sampling by the optional imaging system 111. The passage 304 has an inlet (opening) and an outlet (opening) for the agricultural material to be sampled or analyzed by the optional imaging system 111. In one example, the optional imaging system 111 is analogous to system 11 and may include the same or similar components as system 11 described in this document. The optional imaging system 111 is indicated as optional by the dashed lines in FIG. 8. The optional imaging system 111 receives the undesired portion of agricultural material and takes collected images for analysis by the controller 603 or another electronic controller. The imaging system 111 may be connected to the controller 603 or another electronic controller via a transmission line 651 or data bus. The controller 603 can process images of the undesired portion of the agricultural material to provide data on or more characteristics of the undesired portion of the agricultural material, such as moisture, volume, or other parameters. It can be appreciated by one of ordinary skill in the art that an imaging system (e.g., 11 and/or 111) could be positioned at any number of locations on a harvester to collect images of an agricultural material.

Combine system 100 also includes an engine compartment 14 configured to house one or more engines and engine components for powering the various drives and motors within the combine system 100. The combine system 100 may include fewer, or additional, components than specifically illustrated in FIG. 8 and still be able to achieve the features described herein.

In one example, the elevator 12 comprises an auger 148 that rotates to move agricultural material upward in the elevator 12 and outward toward a discharge end 13 of the chute. In another example, a series of carriers or paddles are movably attached to an elevator drive (e.g., elevator chain) to convey agricultural material upward in the elevator 12 and outward toward a discharge end 13 of the chute.

In one configuration, the imaging device 116 may comprise a video recorder configured to record agricultural material that enter the passage 104 (FIG. 4) or a sampling receptacle so that the recording may be analyzed by a video processing unit comprised of a data processor 604, a data storage device 607 (e.g., memory), and video processing software (608, 609, 610) stored on the memory and executed by the data processor 604. The analysis of the recording may identify physical characteristics of grain that enter the sampling receptacle such as damage to the agricultural material (e.g., broken kernels or damaged kernels).

Figure 9:
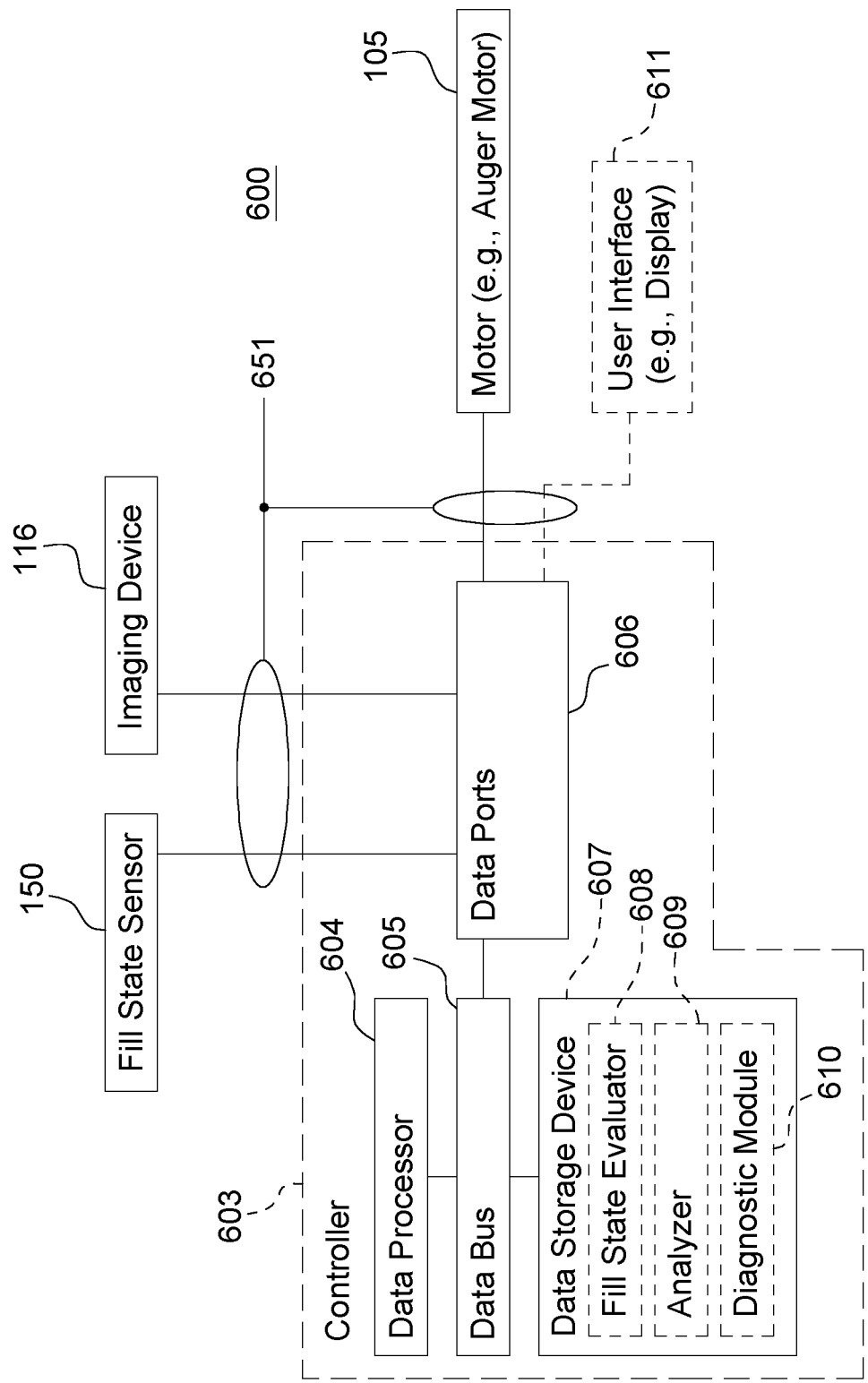
FIG. 9 is a block diagram of the electrical components of the system.

FIG. 9 is a block diagram of the electrical components of the system. A fill state sensor 150 and an imaging device 116 are coupled to a controller 603 via one or more transmission lines 651 (e.g., data bus, wires, cable, or optical fiber). Similarly, the motor 105 (e.g., auger motor) is coupled to the controller 603 via one or more transmission lines 603. In one example, the controller 603 comprises an electronic data processor 604, one or more data ports 606, and a data storage device 607 that coupled to or communicate via a data bus 605. An optional user interface 611 (e.g., display) may be coupled to the controller 603 via one or more data ports 606. The optional nature of the user interface 611 is indicated by the dashed lines and may be deleted from certain configurations.

In one example, the electronic data processor 604 comprises a microprocessor, a microcontroller, an application specific integrated circuit (ASIC), a digital signal processor, a programmable logic array, or another device for processing or manipulating data. The data storage device 607 may comprise electronic memory, non-volatile random access memory, an optical storage device, a magnetic storage device, a hard disk, or any other device for storing data. The user interface 611 may comprise one or more of the following: a display (e.g., touch-screen display), a keypad, a keyboard, a pointing device (e.g., electronic mouse), or a portable computer.

In one illustrative configuration, the data storage device 607 may store one or more of the following software modules for execution by the data processor 604: fill state evaluator 608, analyzer 609, and diagnostic module 610 (e.g., clean alert message generator). Each of the above software modules may comprise executable software instructions, libraries, data or other data structures for processing by the data processor 604.

In one example, a fill state sensor 150 is coupled to a controller 603, or a data port 606 of the controller 603 to provide fill state data on the fill state of passage 104 for triggering of image capture or collection by the imaging device 116. The controller 603 may receive images or image data from the imaging device 116 for processing or analysis via the data port 606. The controller 603 may send command data to the imaging device 116 to begin collection of one or more images or to cease collection of images based on data from the fill state sensor 150, fill state evaluator 608, analyzer 609, or the diagnostic module 610 (e.g., clean alert message generator). In certain configurations, the analyzer 609 may provide data about the characteristic or attributes of the agricultural material (e.g., harvested agricultural material) to an operator of the combine system 100 or harvesting machine via a user interface 611 (e.g., display). The diagnostic module 610 may provide a clean alert message to the operator via the user interface 611 to warn or alter the operator to clean the passage 104, the window 118, or both to improve performance or accuracy of the images of the imaging device 116, and associated analysis of attributes and characteristics by the analyzer 609.

In one example, the controller 603 may comprise a set of one or more electronic controllers or computers that can communicate with each other via a vehicle data bus 605 (e.g., controller area network, Ethernet or another data bus) via data ports (e.g., 606); each electronic controller may comprise a data processor 604, data storage device 607, and data port 606 coupled to a data bus 605. For example, the controller 603 controls the auger 148 or its auger motor 105 to be in a disabled state or inactive state, based on data or signals from a fill state sensor 150, until: (1) the passage 104 is filled with agricultural material to a certain threshold level (e.g., greater than or equal to ninety-five percent (95%) of the surface area of the image, the window 118 or the translucent plate), (2) sufficient images of the agricultural material are taken for evaluation, or (3) both. The full state of the passage 104 can be detected by a fill state sensor 150, such as a capacitive sensor, or by a fill state evaluator 608 that estimates the density or volume of agricultural material in the image or the whether the agricultural material in the image covers a minimum surface area of the field of view or the window 118 or of the total window surface area 122 (e.g., length 199 multiplied by width 197).

An auger 148 or conveyer is in communication with the outlet 110 and the elevator output region 119 for moving grain from the passage 104 into an elevator 12 of a combine or harvesting machine. The auger 148 or conveyer is driven, directly or indirectly, by the auger motor 105, such as an electric auger motor 105. A fill state sensor 150 (e.g., capacitive sensor) is at near a top of the passage 104 to detect the density or volume of the agricultural material to determine whether the passage 104 is filled with agricultural material. If the fill state sensor 150 or fill state evaluator 608 sends a data message or signal indicative of a full state or sufficiently full state, the controller 603 (e.g., or set of one or more controllers) or data processor 604 can trigger the imaging device 116 to take images of the agricultural material through the window 118 or translucent plate and, after the images are collected for a sampled portion of the agricultural material, to activate the auger 148 (or auger motor 105) to transfer or release material from the passage 104 to an elevator 12 of a combine or harvesting machine (e.g., to prepare the passage 104 for a next filling and next image collection by the imaging device 116).

In an alternate example, the fill state sensor 150 or fill state evaluator 608 may be omitted from the system and the data processor 604 can trigger at regular intervals (e.g., periodically) the imaging device 116 to take images of agricultural material, while the auger motor 105 for the auger 148 is controlled (e.g., activated at regular intervals) by a set of controllers 603 without data input from the fill state sensor 150 or the fill state evaluator 608.

In one configuration, the imaging device 116 collects images of the agricultural material in the passage 104 if the imaging device 116 determines that the field of view associated with the window 118 is filled with agricultural material above a certain threshold density level. The threshold density level is approximately ninety-five percent (95%) of the image area is occupied with agricultural material, in one example.

The imaging device 116 collects images of the agricultural material in the passage 104 to evaluate an attribute of the agricultural material, where the attribute is at least one of moisture, broken kernels, damaged kernels, protein content, oil content or foreign matter contamination, among other things.

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the systems, methods, processes, apparatuses and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various examples of the systems, apparatuses, devices, methods and/or processes via the use of block diagrams, schematics, flowcharts, examples and/or functional language. Insofar as such block diagrams, schematics, flowcharts, examples and/or functional language contain one or more functions and/or operations, it will be understood by those within the art that each function and/or operation within such block diagrams, schematics, flowcharts, examples or functional language can be implemented, individually and/or collectively, by a wide range of hardware, software, firmware, or virtually any combination thereof. In one example, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the examples disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of a skilled artisan in light of this disclosure. In addition, those skilled in the art will appreciate that the mechanisms of the subject matter described herein are capable of being distributed as a program product in a variety of forms, and that an illustrative example of the subject matter described herein applies regardless of the signal bearing medium used to carry out the distribution. Examples of a signal bearing medium include, but are not limited to, the following: a computer readable memory medium such as a magnetic medium like a floppy disk, a hard disk drive, and magnetic tape; an optical medium like a Compact Disc (CD), a Digital Video Disk (DVD), and a Blu-ray Disc; computer memory like random access memory (RAM), flash memory, and read only memory (ROM); and a transmission type medium such as a digital and/or an analog communication medium like a fiber optic cable, a waveguide, a wired communications link, and a wireless communication link.

The herein described subject matter sometimes illustrates different components associated with, comprised of, contained within or connected with different other components.

It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two or more components herein combined to achieve a particular functionality can be seen as "associated with" each other such that the desired functionality is achieved, irrespective of architectures or intermediate components. Likewise, any two or more components so associated can also be viewed as being "operably connected", or "operably coupled", to each other to achieve the desired functionality, and any two or more components capable of being so associated can also be viewed as being "operably couplable", to each other to achieve the desired functionality. Specific examples of operably couplable include, but are not limited to, physically mateable and/or physically interacting components, and/or wirelessly interactable and/or wirelessly interacting components, and/or logically interacting and/or logically interactable components.

Unless specifically stated otherwise or as apparent from the description herein, it is appreciated that throughout the present disclosure, discussions utilizing terms such as "accessing," "aggregating," "analyzing," "applying," "brokering," "calibrating," "checking," "combining," "communicating," "comparing," "conveying," "converting," "correlating," "creating," "defining," "deriving," "detecting," "disabling," "determining," "enabling," "estimating," "filtering," "finding," "generating," "identifying," "incorporating," "initiating," "locating," "modifying," "obtaining," "outputting," "predicting," "receiving," "reporting," "retrieving," "sending," "sensing," "storing," "transforming," "updating," "using," "validating," or the like, or other conjugation forms of these terms and like terms, refer to the actions and processes of a control unit, computer system or computing element (or portion thereof) such as, but not limited to, one or more or some combination of: a visual organizer system, a request generator, an Internet coupled computing device, a computer server, etc. In one example, the control unit, computer system and/or the computing element may manipulate and transform information and/or data represented as physical (electronic) quantities within the control unit, computer system's and/or computing element's processor(s), register(s), and/or memory(ies) into other data similarly represented as physical quantities within the control unit, computer system's and/or computing element's memory(ies), register(s) and/or other such information storage, processing, transmission, and/or display components of the computer system(s), computing element (s) and/or other electronic computing device(s). Under the direction of computer-readable instructions, the control unit, computer system(s) and/or computing element(s) may carry out operations of one or more of the processes, methods and/or functionalities of the present disclosure.

Those skilled in the art will recognize that it is common within the art to implement apparatuses and/or devices and/or processes and/or systems in the fashion(s) set forth herein, and thereafter use engineering and/or business practices to integrate such implemented apparatuses and/or devices and/or processes and/or systems into more comprehensive apparatuses and/or devices and/or processes and/or systems. That is, at least a portion of the apparatuses and/or devices and/or processes and/or systems described herein can be integrated into comprehensive apparatuses and/or devices and/or processes and/or systems via a reasonable amount of experimentation.

Although the present disclosure has been described in terms of specific examples and/or embodiments and applications, persons skilled in the art can, considering this teaching, generate additional examples and/or embodiments without exceeding the scope or departing from the spirit of the present disclosure described herein. Accordingly, it is to be understood that the drawings and description in this disclosure are proffered to facilitate comprehension of the present disclosure and should not be construed to limit the scope thereof.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

It should also be noted that the different examples described herein can be combined in different ways. That is, parts of one or more examples can be combined with parts of one or more other examples. All of this is contemplated herein.

Example 1 is a system for evaluating an agricultural material, the system comprising:
  a housing having a passage in or through an interior of the housing with an inlet for receiving the agricultural material and an outlet for outputting the agricultural material;
  a wall opening in a wall of the passage; and
  an imaging device with a removable portion, the removable portion having at least one of a moisture absorbing material, a heat source and an anti-fog agent, the removable portion acting to reduce obscuring of an associated window of the imaging device.

Example 2 is the system for evaluating the agricultural material of any or all previous examples and further comprising wherein the removable portion is removable without disassembly of the imaging device and acts to resist fogging on the window of the imaging device.

Example 3 is the system for evaluating the agricultural material of any or all previous examples and further comprising wherein the removable portion is removable without disassembly of the imaging device and acts to prevent corrosion of internal components of the imaging device.

Example 4 is the system for evaluating the agricultural material of any or all previous examples and further comprising wherein the moisture absorbing material is a desiccant contained within a cartridge attached to the removable portion.

Example 5 is the system for evaluating the agricultural material of any or all previous examples and further comprising wherein the cartridge has an indicator representing the life of the desiccant contained within the cartridge.

Example 6 is the system for evaluating the agricultural material of any or all previous examples and further comprising wherein the desiccant is an orange indicating silica gel, the orange indicating silica gel providing a visual indicator of the remaining life.

Example 7 is the system for evaluating the agricultural material of any or all previous examples and further comprising wherein the heat source is an electrically powered heating coil associated with the removable portion and the window of the imaging device.

Example 8 is the system for evaluating the agricultural material of any or all previous examples and further comprising wherein the heating coil heats at least one of the window and the housing within which agricultural material passes.

Example 9 is the system for evaluating the agricultural material of any or all previous examples and further comprising wherein the anti-fog agent is an anti-fog film activated by the removable portion within the imaging device.

Example 10 is the system for evaluating the agricultural material of any or all previous examples and further comprising wherein the imaging device collects images of the agricultural material in the passage to evaluate an attribute of the agricultural material, wherein the attribute is at least one of moisture, broken kernels, damaged kernels, protein content, oil content and foreign matter contamination.

Example 11 is the system for evaluating the agricultural material of any or all previous examples and further comprising wherein the imaging device collects images of the agricultural material in the passage if the level of agricultural material occupying a field of view or a surface area associated with the window exceeds a threshold level.

Example 12 is the system for evaluating the agricultural material of any or all previous examples and further comprising wherein the window has rounded corners to prevent the window from cracking in response to thermal stress.

Example 13 is an apparatus for evaluating an agricultural material, the apparatus comprising:
a removable portion configured to interface with an imaging device, the removable portion having at least one of a moisture absorbing material, a heat source, and an anti-fog agent to reduce fogging of a window of the imaging device due to a temperature differential between the agricultural material and the imaging device.

Example 14 is a system for evaluating an agricultural material, the system comprising:
an imaging device having a window located within a border, wherein the imaging device is pivotally mounted for rotation with respect to a housing through which the agricultural material passes such that in a closed state the border rests on, engages or interlocks with a wall opening in the housing, and in an open state the border exposes the wall opening and the interior of the housing; and
a removable portion interfacing with the imaging device, the removable portion having at least one of a moisture absorbing material, a heat source, and an anti-fog agent within the removable portion.

Example 15 is the system for evaluating the agricultural material of any or all previous examples and further comprising wherein the open state a surface of the window that faces the interior of the housing is exposed to facilitate cleaning of debris or other material from the surface of the window.

Example 16 is the system for evaluating the agricultural material of any or all previous examples and further comprising a hinge comprising a first hinge portion and a second hinge portion, the first hinge portion secured to the imaging device and the second hinge portion secured to the housing.

Example 17 is the system for evaluating the agricultural material of any or all previous examples and further comprising a latch for engaging a keeper to lock the imaging device to the housing in the closed state.

Example 18 is the system for evaluating the agricultural material of any or all previous examples and further comprising wherein the border is generally rectangular and protrudes from the imaging device.

Example 19 is the system for evaluating the agricultural material of any or all previous examples and further comprising wherein the imaging device collects images of the agricultural material in the housing to evaluate an attribute of the agricultural material, wherein the attribute is at least one of moisture, broken kernels, damaged kernels, protein content, oil content and foreign matter contamination.

Example 20 is the system for evaluating the agricultural material of any or all previous examples and further comprising wherein the imaging device collects images of the agricultural material in the housing if the level of the agricultural material occupying a field of view or a surface area associated with the window exceeds a threshold level.

Example 21 is the system for evaluating the agricultural material of any or all previous examples and further comprising wherein the threshold level is approximately 95%.

Example 22 is the system for evaluating the agricultural material of any or all previous examples and further comprising wherein the window has rounded corners to prevent the window from cracking in response to thermal stress.

Example 23 is the system for evaluating the agricultural material of any or all previous examples and further comprising wherein the imaging device further comprises:
an image sensor facing the window to collect image data of the agricultural material in a passage; and
a plurality light sources spaced apart from the image sensor such that the window is illuminated from radiation emitted from the light sources and direct reflections of the radiation do not impinge upon the image sensor to reduce glare or glare-related distortion in the collected image data.

Example 24 is the system for evaluating the agricultural material of any or all previous examples and further comprising wherein the imaging device further comprises a circuit board, the circuit board connected to a communications port the removable portion.

What is claimed is:

1. A system for evaluating an agricultural material, the system comprising:
a housing having a passage in or through an interior of the housing with an inlet for receiving the agricultural material and an outlet for outputting the agricultural material;
a wall opening in a wall of the passage; and
an imaging device, the imaging device including a removable portion, the removable portion acting to reduce obscuring of a window of the imaging device, connected by a first fastener and a seal to the imaging device, and removable without disassembly of the imaging device, and having
a heat source, the heat source to include an electrically powered heating coil to heat the agricultural material to reduce a temperature differential between the imaging device and the agricultural material to reduce fogging of the window.

2. The system of claim 1, wherein the removable portion acts to resist fogging on the window of the imaging device by dispersing an anti-fog agent from the removable portion.

3. The system of claim 1, wherein the removable portion acts to prevent corrosion of internal components of the imaging device.

4. The system of claim 1, wherein the removable portion further includes a moisture absorbing material in a replaceable cartridge held in place by an anti-rotation bracket and a second fastener, wherein a base plate of the removable portion is to include an aperture through which air can circulate between an internal cavity of the removable portion and an internal cavity of the imaging device, and wherein the moisture absorbing material is a desiccant contained within the replaceable cartridge attached to the removable portion.

5. The system of claim 4, further including an indicator corresponding to a life of the desiccant contained within the replaceable cartridge.

6. The system of claim 5, wherein the desiccant is a color-indicating silica gel, the color-indicating silica gel providing a visual indicator of the life of the color-indicating silica gel.

7. The system of claim 1, wherein the electrically powered heating coil heats at least a periphery of the window of the imaging device.

8. The system of claim 1, wherein the imaging device collects images of the agricultural material in the passage to evaluate an attribute of the agricultural material, wherein the attribute is at least one of moisture, broken kernels, damaged kernels, protein content, oil content and foreign matter contamination.

9. The system of claim 1, wherein the imaging device collects images of the agricultural material in the passage if a level of the agricultural material occupying a field of view or a surface area associated with the window exceeds a threshold level.

10. The system of claim 1, wherein the window has rounded corners to prevent the window from cracking in response to thermal stress.

11. The system of claim 1, wherein the imaging device further includes a circuit board, the circuit board to include a humidity sensor.

12. An apparatus for evaluating an agricultural material, the apparatus comprising
a removable portion configured to interface with an imaging device, the removable portion removable from the imaging device without disassembly of the imaging device and connected by a fastener and a seal to the imaging device, the removable portion acting to reduce fogging of a window of the imaging device via,
a heat source, the heat source to include an electrically powered heating coil to heat the agricultural material to reduce a temperature differential between the imaging device and the agricultural material to reduce fogging of the window.

13. A system for evaluating an agricultural material, the system comprising:
an imaging device having a window located within a border, wherein the imaging device is pivotally mounted for rotation with respect to a housing through which the agricultural material passes such that, in a closed state, the border rests on, engages or interlocks with a wall opening in the housing, and, in an open state, the border exposes the wall opening and an interior of the housing; and
a removable portion interfacing with the imaging device, the removable portion removable from the imaging device without disassembly of the imaging device, the removable portion connected by a fastener and a seal to the imaging device, and the removable portion having a heat source, the heat source to include an electrically powered heating coil to heat the agricultural material to reduce a temperature differential between the imaging device and the agricultural material to reduce fogging of the window.

14. The system of claim 13, wherein, in the open state, a surface of the window that faces the interior of the housing is exposed to facilitate cleaning of debris or other material from the surface of the window.

15. The system of claim 13, further including a hinge including a first hinge portion and a second hinge portion, the first hinge portion secured to the imaging device and the second hinge portion secured to the housing.

16. The system of claim 13, further including a latch for engaging a keeper to lock the imaging device to the housing in the closed state.

17. The system of claim 13, wherein the border is generally rectangular and protrudes from the imaging device.

18. The system of claim 13, wherein the imaging device collects images of the agricultural material in the housing to evaluate an attribute of the agricultural material, wherein the attribute is at least one of moisture, broken kernels, damaged kernels, protein content, oil content and foreign matter contamination.

19. The system of claim 13, wherein the imaging device collects images of the agricultural material in the housing if a level of the agricultural material occupying a field of view or a surface area associated with the window exceeds a threshold level.

20. The system of claim 19, wherein the threshold level is approximately 95%.

21. The system of claim 13, wherein the window has rounded corners to prevent the window from cracking in response to thermal stress.

22. The system of claim 13, wherein the imaging device further includes:
an image sensor facing the window to collect image data of the agricultural material in a passage; and
a plurality of light sources spaced apart from the image sensor such that the window is illuminated from radiation emitted from the plurality of light sources and direct reflections of the radiation do not impinge upon the image sensor to reduce glare or glare-related distortion in the image data.

23. The system of claim 22, wherein the imaging device further includes a circuit board, the circuit board connected to a communications port on the removable portion.

* * * * *

UNITED STATES PATENT AND TRADEMARK OFFICE
CERTIFICATE OF CORRECTION

| | | |
|---|---|---|
| PATENT NO. | : 12,259,376 B2 | Page 1 of 1 |
| APPLICATION NO. | : 17/304979 | |
| DATED | : March 25, 2025 | |
| INVENTOR(S) | : Culpepper et al. | |

It is certified that error appears in the above-identified patent and that said Letters Patent is hereby corrected as shown below:

On the Title Page

Under item (73) Assignee, Delete "Deer & Company, Moline, IL (US)" and Insert --Deere & Company, Moline, IL (US)--.

Signed and Sealed this
Thirteenth Day of May, 2025

Coke Morgan Stewart
*Acting Director of the United States Patent and Trademark Office*